(12) United States Patent
Nielan et al.

(10) Patent No.: US 12,095,203 B2
(45) Date of Patent: Sep. 17, 2024

(54) SYSTEM AND METHOD FOR SELF-ALIGNING HUB CONNECTOR

(71) Applicants: BAXTER INTERNATIONAL INC., Deerfield, IL (US); BAXTER HEALTHCARE SA, Glattpark (CH)

(72) Inventors: Greg Nielan, Elma, NY (US); James Rowe, Dandenong (AU); Vincent Khau, South Yarra (AU); David Gorgi, Schaumburg, IL (US); Jiri Slaby, Buffalo Grove, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 374 days.

(21) Appl. No.: 17/566,117

(22) Filed: Dec. 30, 2021

(65) Prior Publication Data
US 2022/0209461 A1 Jun. 30, 2022

Related U.S. Application Data

(60) Provisional application No. 63/132,060, filed on Dec. 30, 2020.

(51) Int. Cl.
*H01R 13/00* (2006.01)
*H01R 13/52* (2006.01)
(Continued)

(52) U.S. Cl.
CPC ....... *H01R 13/631* (2013.01); *H01R 13/5219* (2013.01); *H01R 13/73* (2013.01);
(Continued)

(58) Field of Classification Search
CPC .. H01R 13/631; H01R 13/5219; H01R 13/73; H01R 43/26
See application file for complete search history.

(56) References Cited

U.S. PATENT DOCUMENTS

| 5,746,976 A | 5/1998 | Yamada et al. |
| 8,795,593 B2 * | 8/2014 | Nichols .................. G01N 35/04 422/65 |

(Continued)

OTHER PUBLICATIONS

First Office Action No. 3471 for Colombian Application No. NC2023/0008687 dated Feb. 26, 2024.

*Primary Examiner* — Phuong Chi Thi Nguyen
(74) *Attorney, Agent, or Firm* — K&L Gates LLP

(57) ABSTRACT

A system and method for self-aligning and connecting a device to a modular rack. The system includes a device comprising a connector receptacle configured to receive a connector plug, a connector seal and a bracket fixed to the device, a modular rack comprising the connector plug, a connector shell seal and a shelf configured to receive the bracket and guide the shelf in a plurality of directions. When the bracket of the device is inserted into the shelf of the modular rack, the shelf travels in the plurality of directions to self-align the connector plug of the modular rack to the connector receptacle of the device to ensure engagement of the connector plug to the connector receptacle. The connector seal is biased towards the connector shell seal to create a seal and ensure engagement of the connector plug relative to the connector receptacle.

20 Claims, 10 Drawing Sheets

(51) Int. Cl.
  *H01R 13/631*   (2006.01)
  *H01R 13/73*    (2006.01)
  *H01R 43/26*    (2006.01)
  *A61M 5/142*    (2006.01)
  *F16L 37/00*    (2006.01)

(52) U.S. Cl.
  CPC ............ *H01R 43/26* (2013.01); *A61M 5/142* (2013.01); *F16L 37/00* (2013.01)

(56) References Cited

U.S. PATENT DOCUMENTS

| | | | |
|---|---|---|---|
| 9,320,166 B1* | 4/2016 | Marr | H05K 7/14 |
| 9,410,976 B2* | 8/2016 | Bailey | G01N 30/16 |
| 10,318,441 B2* | 6/2019 | Inoue | G01N 33/0037 |
| 10,454,229 B2 | 10/2019 | Wolff | |
| 11,052,742 B2* | 7/2021 | Murphy | B60K 1/04 |
| 2014/0321096 A1 | 10/2014 | Kajackas | |

\* cited by examiner

SYSTEM AND METHOD FOR SELF-ALIGNING HUB CONNECTOR

CROSS-REFERENCE TO RELATED APPLICATION

This application claims the benefit of priority of U.S. Provisional Patent Application No. 63/132,060 filed on Dec. 30, 2020. This application is being filed on the same day with an international patent application entitled "SYSTEM AND METHOD FOR SELF-ALIGNING HUB CONNECTOR" claiming the benefit of priority of U.S. Provisional Patent Application No. 63/132,060 filed on Dec. 30, 2020. The contents of all of the above documents are incorporated by reference as if fully set forth herein.

BACKGROUND

The present disclosure provides new and innovative systems and methods for connecting a device to a modular rack. Devices such as medical devices (e.g., medical pump(s)) may positioned or organized in a rack. Generally, medical pumps have been developed to provide controlled drug infusion such that the drug can be administered at a precise rate that maintains the drug concentration within a therapeutic margin to prevent administration of unnecessary or possibly toxic concentration margins or ranges. For example, the medical pumps are adapted to provide appropriate drug delivery to a patient at a controllable rate (without requiring frequent attention for a clinician).

Medical pumps may facilitate administration of intravenous therapy to patients both in and outside of a clinical setting. Outside a clinical setting, patients may return to substantially normal lives, provided that they receive periodic or continuous intravenous administration of medication. Among the types of therapies requiring periodic or continuous intravenous administration include (but are not limited to) antibiotic therapy, chemotherapy, pain control therapy, nutritional therapy, and several other types known by those skilled in the art. Patients may receive multiple daily therapies, and certain medical conditions require infusion of drugs in solution over relatively short periods (e.g., from 30 minutes to two hours). Based on the frequency and duration of the infusions, increasingly lightweight, portable or ambulatory infusion pumps have been developed that may be worn by a patient and that are capable of administering a continuous supply of medication at a desired rate or at predetermined and scheduled intervals.

Configurations of infusion pumps include elastomeric pumps, which squeeze solution from flexible containers, such as balloons, into IV tubing for delivery to the patient. Alternatively, spring-loaded pumps pressurize the solution containers or reservoirs. Certain pump designs utilize cartridges containing flexible compartments that are squeezed by pressure rollers for discharging the solutions. Infusion pumps utilizing syringes are also known wherein a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls. Additionally, some medical devices, such as infusion pumps are portable while others are larger and may remain stationary. Alternatively, medical devices such as infusion pumps may be moved about in a hospital setting in either a cart, rack or hub.

Regardless of the size and type of medical pump or medical device, most medical devices require a power source (either internal or external) to operate. For example, medical devices such as infusion pumps may be placed on or positioned within a rack (e.g., a modular rack), sometimes called hubs, which may be wired to provide power to the medical devices (e.g., pumps) placed on or within the racks. Medical devices (e.g., pumps) designed to be placed on a modular rack may have a connection receptacle located on the exterior of the medical device that connects to a connector plug located on the rack itself. This connection may supply the medical device (e.g., pump) with power to operate. Additionally, if the necessary wiring is provided, this connection may facilitate communication between the medical device (e.g., pump) and the rack. However, in order for the medical device (e.g., pump) to operate as intended, proper alignment of the connection between the medical device and rack is necessary to ensure sufficient engagement of the connection(s) between the medical device and the rack. Otherwise, the medical device may not receive power to operate, communication(s) between the medical device and the rack may be disrupted, and/or the medical device may otherwise not operate as intended.

Existing techniques for connecting a medical device (e.g. a pump) to a modular rack have several disadvantages. For example, one existing technique for connecting a medical device (e.g., a pump) to a modular rack includes manually lifting the pump into position while viewing the connection(s), connector(s) or connection interface(s) to ensure proper engagement between the connectors. This existing technique, however, has several drawbacks because the clinician may be unable to view one or more of the connection(s) or connection interfaces. For example, the location of the connection(s), connectors or connection interfaces may hinder a clinician's view, e.g., when a connection interface is positioned on a back side of a medical device. Furthermore, several medical devices (e.g., pumps) may be stacked on top of each other when placed on or within a modular rack, which creates additional congestions and therefore may further hinder a clinician's line-of-sight or ability to properly view the respective connection interfaces. The inability to properly observe connection interface(s) and the coupling of such interfaces may prevent the clinician from ensuring proper connection of the medical devices (e.g., pumps) on a given rack. In the course of a day, a clinician may connect and inspect the connections of several medical devices (e.g., pumps), and the existing techniques of manually connecting and physically observing the connections to ensure proper engagement is both time consuming and logistically burdensome for clinicians. These drawbacks may be further augmented and manifested based on the quantity and size of medical devices (e.g., pumps) a clinician manually connects and inspects throughout the day.

Accordingly, a system and/or method for connecting a medical device (e.g., pump) to a modular rack that ensures proper engagement of connections without the need to have the connections manually inspected is desired.

SUMMARY

The present disclosure provides new and innovative systems and methods for passively connecting a device to a modular rack. In various examples described herein, the device may be a medical device, such as a pump (e.g., infusion pump). However, it should be appreciated that that a pump, such as an infusion pump, is provided as a non-limiting example of a medical device that may benefit from the techniques disclosed herein. The modular rack in various embodiments is configured to be electrified and capable of holding at least one medical pump. It should be appreciated that the rack is in various embodiments, any type of electrified modular rack, or any other suitable device capable of holding and providing a connection to a device.

The provided system includes a modular rack configured with an electrified wiring harness, a connector plug, a connector shell seal and a guiding system. The guiding system includes a shelf to receive a bracket, rails to guide and retain the bracket and mechanical means to move the shelf in a plurality of directions, facilitating tri-axial self-alignment of the shelf in relation to the connector plug. The connector plug is disposed within the connector seal shell and spatial volume is provided adjacent to the connector plug within the connector seal shell to allow for freedom of movement during self-alignment. The provided system also includes a bracket that is configured to attach to the bottom of a device. For example, the device is a medical pump with a connector respectable and a connector seal located on the exterior of the medical pump. The connector receptacle sits within the connector seal and is configured to receive a connector plug. The connector seal is biased towards the connector shell seal to ensure engagement.

Once the bracket is attached to the device and the device-bracket couplet is place on the shelf of the rack, the mechanical means of the guiding system moves the shelf and the device on it, in a plurality of directions. The guiding system facilitates tri-axial self-alignment of the connector receptacle of the device in relation to the connector plug of the rack. The guiding system provides for passive connection of the device to the rack while ensuring proper engagement of the connector plug to the connector receptacle. As a result of the system providing several shelves, multiple devices may be connected in a passive manner using the disclosed guiding system.

In another aspect of the present disclosure, which may be used in combination with any other aspect or combination of aspects listed herein, a self-aligning connection system includes a device comprising a connector receptacle configured to receive a connector plug, a connector seal and a bracket fixed to the device, a modular rack comprising the connector plug, a connector shell seal and a shelf configured to receive the bracket and guide the shelf in a plurality of directions.

In another aspect of the present disclosure, which may be used in combination with any other aspect or combination of aspects listed herein, when the bracket of the device is inserted into the shelf of the modular rack, the shelf travels in the plurality of directions to self-align the connector plug of the modular rack to the connector receptacle of the device to ensure engagement of the connector plug to the connector receptacle.

In another aspect of the present disclosure, which may be used in combination with any other aspect or combination of aspects listed herein, a wherein in response to the connector receptacle initiating engagement with the connector plug, the connector plug travels in the plurality of directions to adjust a spatial position in relation to the connector receptacle; and In another aspect of the present disclosure, which may be used in combination with any other aspect or combination of aspects listed herein, when the connector shell seal of the modular rack and the connector seal of the device are aligned, the connector seal is biased towards the connector shell seal to create a seal and ensure engagement of the connector plug relative to the connector receptacle.

In another aspect of the present disclosure, which may be used in combination with any other aspect or combination of aspects listed herein, the connector plug is disposed within the connector shell seal and a spatial volume is provided adjacent to the connector plug within the connector seal shell to allow for freedom of movement during self-alignment.

In another aspect of the present disclosure, which may be used in combination with any other aspect or combination of aspects listed herein, the device is a medical device.

In another aspect of the present disclosure, which may be used in combination with any other aspect or combination of aspects listed herein, the engagement between the device and the modular rack allows for an operable connection of at least one of an electrical connection, a data connection, a gas connection, and a fluid connection.

In another aspect of the present disclosure, which may be used in combination with any other aspect or combination of aspects listed herein, the connector seal is biased towards the connector shell seal to ensure engagement of the connector plug relative to the connector receptacle.

In another aspect of the present disclosure, which may be used in combination with any other aspect or combination of aspects listed herein, the plurality of directions includes an X-direction, a Y-direction and a Z-direction.

In another aspect of the present disclosure, which may be used in combination with any other aspect or combination of aspects listed herein, the self-aligning connection system includes a device comprising a connector receptacle configured to receive a connector plug, a connector seal and a bracket fixed to the device, a modular rack comprising the connector plug, a connector shell seal and a shelf configured to receive the bracket and guide the shelf in a plurality of directions and a guiding system with mechanical means to facilitate the movement of the bracket of the device in relation to the shelf of the modular rack without human intervention.

In another aspect of the present disclosure, which may be used in combination with any other aspect or combination of aspects listed herein, when the bracket of the device is inserted into the shelf of the modular rack, the shelf travels in a plurality of directions to self-align the connector plug of the modular rack to the connector receptacle of the device to ensure engagement of the connector plug to the connector receptacle;

In another aspect of the present disclosure, which may be used in combination with any other aspect or combination of aspects listed herein, in response to the connector receptacle initiating engagement with the connector plug, the connector plug travels in the plurality of directions to adjust a spatial position in relation to the connector receptacle.

In another aspect of the present disclosure, which may be used in combination with any other aspect or combination of aspects listed herein, when the connector shell seal of the modular rack and the connector seal of the device are aligned, the connector seal is biased towards the connector shell seal to create a seal and ensure engagement of the connector plug relative to the connector receptacle.

In another aspect of the present disclosure, which may be used in combination with any other aspect or combination of aspects listed herein, the connector plug is disposed within the connector shell seal and a spatial volume is provided adjacent to the connector plug within the connector seal shell to allow for freedom of movement during self-alignment.

In another aspect of the present disclosure, which may be used in combination with any other aspect or combination of aspects listed herein, the device is a medical device.

In another aspect of the present disclosure, which may be used in combination with any other aspect or combination of aspects listed herein, the engagement between the device and the modular rack allows for an operable connection of at least one of an electrical connection, a data connection, a gas connection, and a fluid connection.

In another aspect of the present disclosure, which may be used in combination with any other aspect or combination of aspects listed herein, the connector seal is biased towards the connector shell seal to ensure engagement of the connector plug relative to the connector receptacle In another aspect of the present disclosure, which may be used in combination with any other aspect or combination of aspects listed herein, the plurality of directions includes an X-direction, a Y-direction and a Z-direction.

In another aspect of the present disclosure, which may be used in combination with any other aspect or combination of aspects listed herein, the shelf of the modular rack includes guide rails that are configured to retain and guide the bracket of the device.

In another aspect of the present disclosure, which may be used in combination with any other aspect or combination of aspects listed herein, a method for connecting a device to a modular rack includes providing the device with a connector receptacle and a connector seal configured to receive a connector plug, attaching a bracket to at least one surface of the device, providing a modular rack with at least one shelf and at least one connector plug to provide an operable connection from the modular rack relative to the device, inserting the bracket of the device in a shelf of the modular rack configured to receive the bracket and providing a guiding system operable with the modular rack with mechanical means to guide and retain the bracket of the device and move the shelf in a plurality of directions, facilitating tri-axial self-alignment of the shelf in relation to the connector plug.

In another aspect of the present disclosure, which may be used in combination with any other aspect or combination of aspects listed herein, the step of providing the device with the connector receptacle and the connector seal configured to receive the connector plug includes, in response to the connector receptacle of the device initiating engagement with the connector plug of the modular rack, the connector plug traveling in a plurality of directions to adjust a spatial position in relation to the connector receptacle to facilitate connection between the device and the modular rack.

In another aspect of the present disclosure, which may be used in combination with any other aspect or combination of aspects listed herein, the method includes biasing the connector seal towards the connector shell seal to ensure engagement of the connector plug relative to the connector receptacle.

In another aspect of the present disclosure, which may be used in combination with any other aspect or combination of aspects listed herein, the operable connection is at least one of an electrical connection, a data connection, a gas connection, and a fluid connection.

In another aspect of the present disclosure, which may be used in combination with any other aspect or combination of aspects listed herein, the method is performed without human intervention.

In another aspect of the present disclosure, which may be used in combination with any other aspect or combination of aspects listed herein, the device is a medical device.

In another aspect of the present disclosure, which may be used in combination with any other aspect or combination of aspects listed herein, the plurality of directions include an X-direction, a Y-direction and a Z-direction.

An additional benefit of the provided system includes decreasing the downtime of the medical pumps due to connection or power source issues, thereby increasing the efficiency of the clinical resources and the value provided by the system.

DETAILED DESCRIPTION

The present disclosure provides systems, methods and techniques for self-aligning connection(s) between a device(s) and a modular rack or hub. The systems, methods and techniques disclosed herein advantageously allow for tri-axial alignment (e.g., auto-alignment or self-alignment) for ensuring proper connection of the device(s) to the rack. The provided systems, methods and techniques may be implemented on medical devices, such as medical pumps (e.g., infusion pumps) to alleviate the burden experienced by clinicians when manually connecting medical devices to modular racks. Specifically, the techniques disclosed herein may advantageously reduce or eliminate the occurrence of improper connections when installing a medical device within a rack or hub. By ensuring proper connections (e.g., via a self-aligning or auto-aligning tri-axial alignment mechanism), the medical devices receive the required power to operate, are able to establish proper communication with the rack and other devices housed in the rack while reducing downtime and increasing efficiency of clinical resources.

Figure 1:
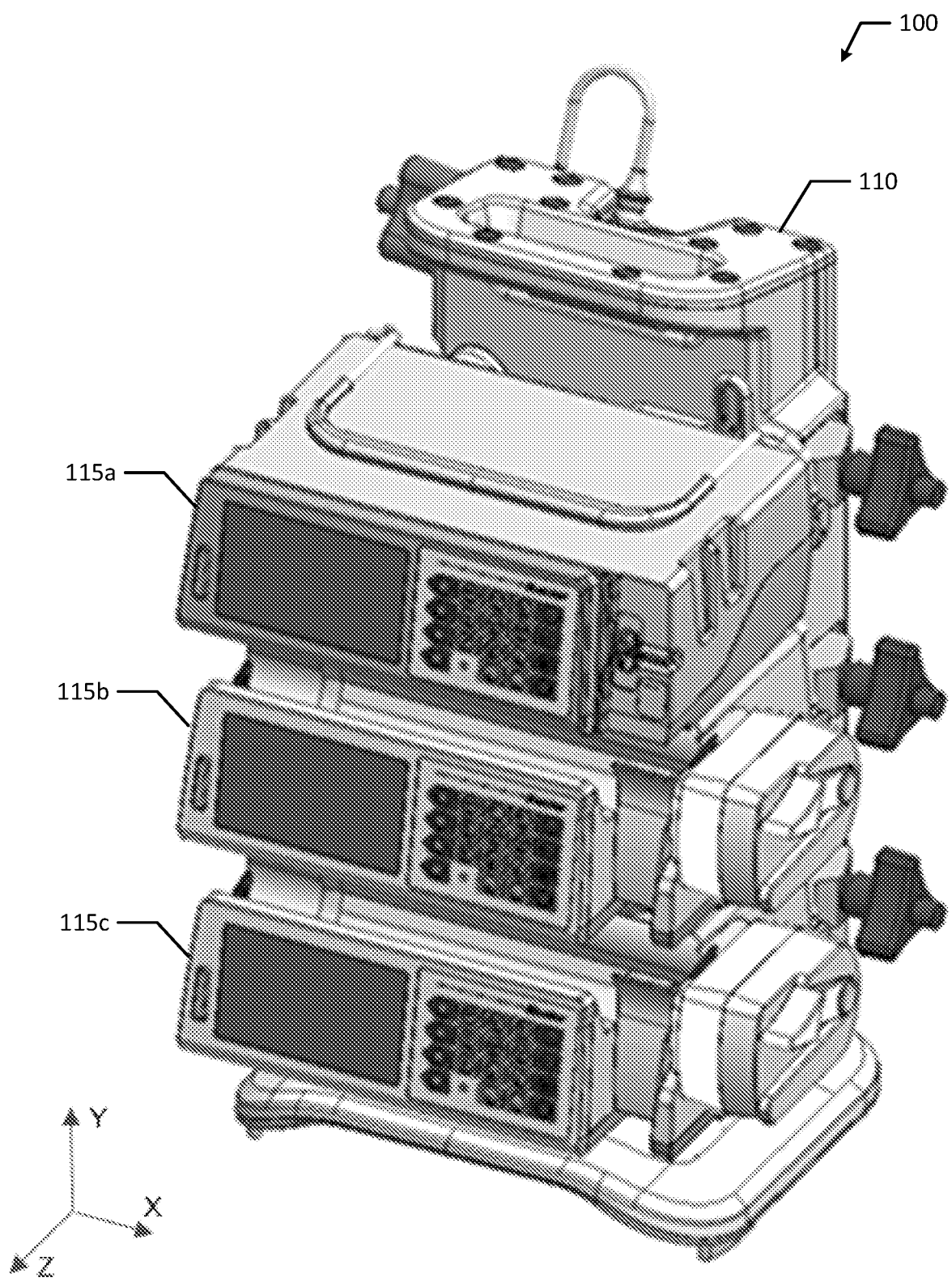
FIG. 1 is a perspective view of an example of a self-aligning connector system with a plurality of devices in a connected position according to an example embodiment of the present disclosure.

FIG. 1 is a perspective view of an example self-aligning connector system 100. As illustrated in FIG. 1, the self-aligning connector system 100 includes a modular rack 110 with a plurality of devices 115a-c poisoned therein (e.g., devices 115a-c are in a connected position). In the illustrated example, the system 100 includes three medical devices 115a-c (e.g., three infusion pumps), however if should be appreciated that the system 100 may be configured to accommodate more than three medical devices. In order for a medical device (e.g., medical device 115a-c, hereinafter referred to generally as medical device 115), such as an infusion pump to establish a proper connection to the rack 110, guidance may be required to align the connections (e.g., connection interfaces on the medical devices 115 as well as the rack 110). Ordinarily, a clinician manually (i) places a medical device 115 (e.g., infusion pump) on a rack 110, (ii) guides the connection interfaces of the medical device 115 towards those of the rack 110, and (iii) actively ensures the connection interfaces are completely engaged. The manual process described above is both time consuming and has the potential for human error. Meanwhile, the techniques disclosed herein alleviate the burden on the clinician and also reduces or eliminates the potential for human error when establishing a connection between a medical device and a rack or hub.

As described in more detail below, both the medical devices 115 and the hub or rack 110 may have assembly tolerances for manufacturability. While these tolerances may be minimized, the resulting assembly tolerance may be insufficient to support self-alignment in the x-direction or the y-direction (e.g., along the X-axis or the Y-axis). Additionally, properly connecting the medical devices 115 and the hub or rack 110 may also depend on gasket compression. For example, self-alignment in the z-direction (e.g., along the Z-axis) may ensure adequate gasket compression with sufficient sealing pressure to prevent a marginal seal between a respective medical device 115 and rack 110.

Figure 2A:
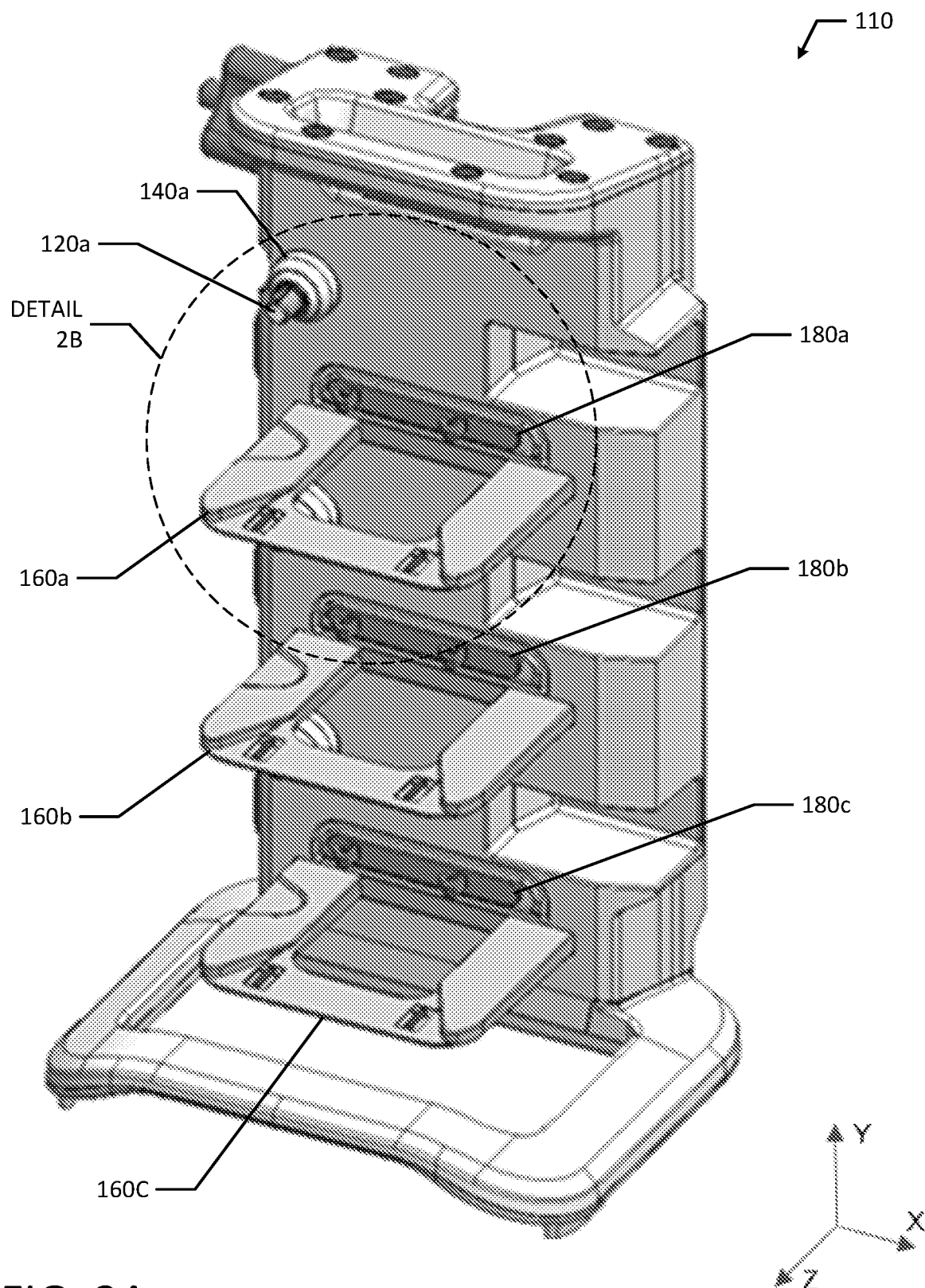
FIG. 2A is a perspective view of an example rack absent any devices in the connected position according to an example embodiment of the present disclosure.

FIG. 2A is a perspective view of the rack 110, which may be rack 110 of FIG. 1, prior to or absent any devices 115 connected to or positioned therein. As shown in FIG. 2, the modular rack 110 may include a connector plug 120a disposed within a connector shell seal 140a. The modular rack 110 may include multiple connector plugs and connector shell seals (e.g., connector plugs 120a-c and connector shell seals 140a-c). The rack 110 may also include at least one shelf 160a-c, hereinafter referred to generally as shelf 160. The shelf 160 may have a planar surface with guide rails that are configured to retain and guide a corresponding mating structure (e.g., bracket 260 illustrated in FIG. 4) fixed to a device 115. A guiding system 180 may be positioned immediately adjacent the shelf 160. The guiding system 180 may include mechanical means for facilitating self-alignment of a device 115 along an X-axis or horizontal plane.

The connector plug 120 is configured to self-align in both the vertical and normal axial directions (e.g., self-align along both of the Y-axis and Z-axis) when the connector plug 120 engages with a corresponding connector receptacle (e.g., connector receptacle 420 illustrated in FIG. 4) of the device 110. When the connector plug 120 is disposed within the connector seal shell 140, spatial volume is provided adjacent to the connector plug 120 within the connector seal shell 140 to allow for freedom of movement during self-alignment.

Figure 2B:
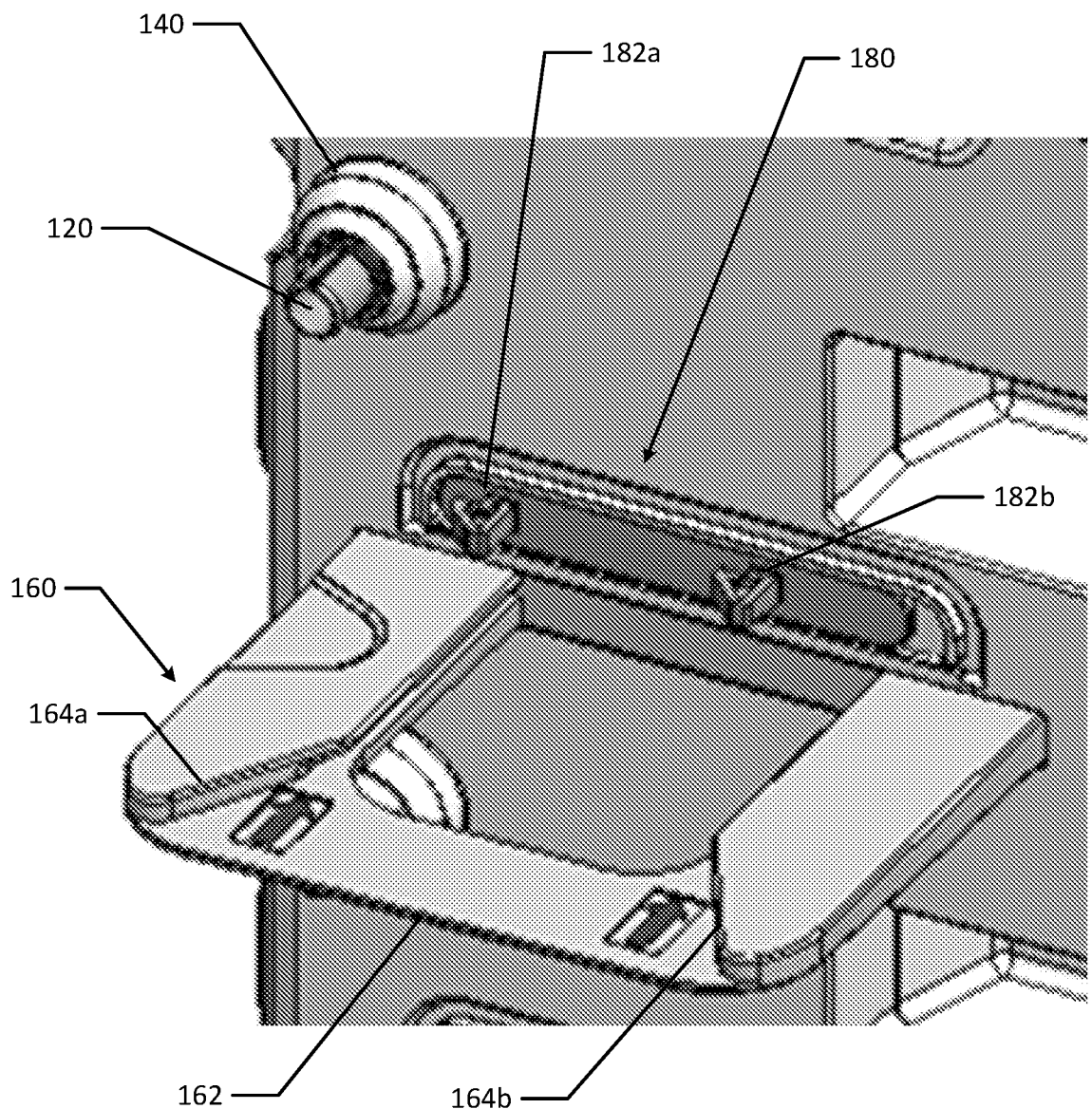
FIG. 2B is a partial detail view of a connection interfaces of the rack according to an example embodiment of the present disclosure.

FIG. 2B is a partial detail view of the portion of the rack 110 that includes the connector plug 120, connector seal shell 140, shelf 160, and guiding system 180. As mentioned above, the shelf 160 may have a planar surface 162 with guide rails 164a and 164b, hereinafter referred to generally as guide rails 164. The shelf 160, the planar surface 162 and/or the guide rails 164 may be configured to retain and guide a corresponding mating structure (e.g., bracket 460 illustrated in FIG. 4) fixed to device 115. The guiding system 180 may be positioned immediately adjacent the shelf 160. The guiding system 180 may include mechanical means for facilitating self-alignment of the device 115 along an X-axis or horizontal plane via shelf 160. Additionally, the guiding system 180 may include retention clips that hold a corresponding medical device 115 on the shelf 160 after the medical device 115 and rack 110 are properly engaged.

The guide rails 164 are adapted to orient the medical device's connector receptacle (e.g., connector receptacle 420 illustrated in FIG. 4) towards the connector plug 120 of the rack 110. For example, the guide rails 164 may assist with aligning the connector plug 120 and the connector receptacle (e.g., connector receptacle 420 illustrated in FIG. 4) prior to engagement of the connector plug 120 and connector receptacle of a corresponding medical device 115. As described in more detail with relation to FIGS. 5A-5D, once the connector receptacle (e.g., connector receptacle 420 illustrated in FIG. 4) starts to engage with the connector plug 120, the connector plug 120 may self-adjust spatially thereby adjusting its special position based on the connector receptacle's axial position thereby ensuring a proper seal between the connector plug 120 and the connector receptacle (e.g., connector receptacle 420 illustrated in FIG. 4). As the medical device 115 and its associated connector receptacle (e.g., connector receptacle 420 illustrated in FIG. 4) are advanced towards the connector plug 120 and the connector shell seal 140, the connector seal (e.g., connector seal 440 illustrated in FIG. 4) may contact and compress the connector plug 120 and/or the connector shell seal 140.

Figure 3A:
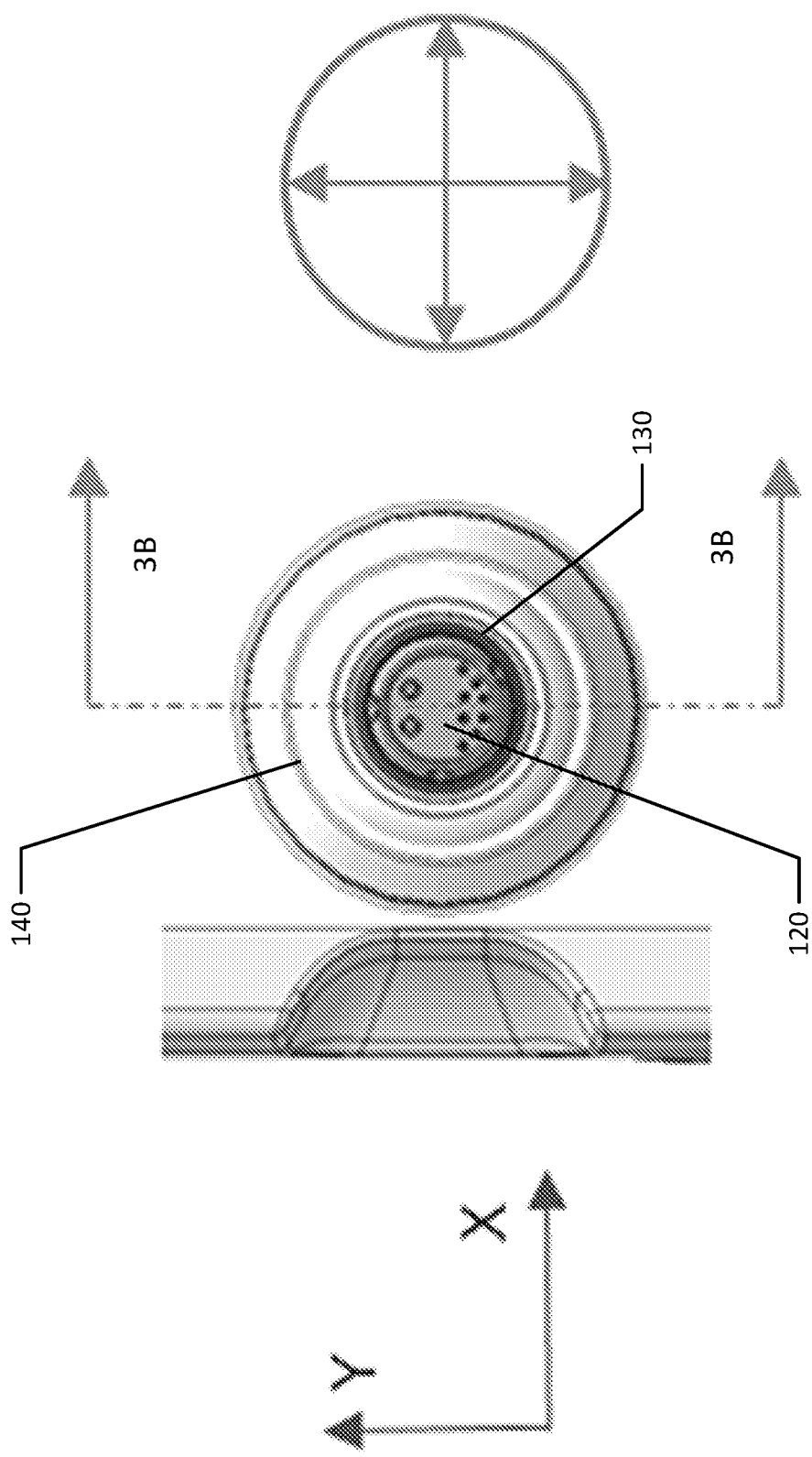
FIG. 3A is a front view of an example connector plug and connector receptacle according to an example embodiment of the present disclosure.

FIG. 3A is a front view of the connector plug 120 and connector shell seal 140. Additionally, FIG. 3A illustrates the various axial directions the connector plug 120 is capable of moving. For example, movement of the connector plug 120 in the X-direction or the Y-direction (e.g., along the X-axis and Y-axis) may be facilitated by the self-aligning connector system of the present disclosure. As shown in FIG. 3A, the connector plug 120 is disposed within connector seal shell 140. The connector plug 120 may be coupled to an outer surface of the rack 110 in such a way that provides flexibility to self-align in 3-dimensional space relative to the connector receptacle (e.g., connector receptacle 420 illustrated in FIG. 4) of the device 115 being place on the rack 110.

Figure 3B:
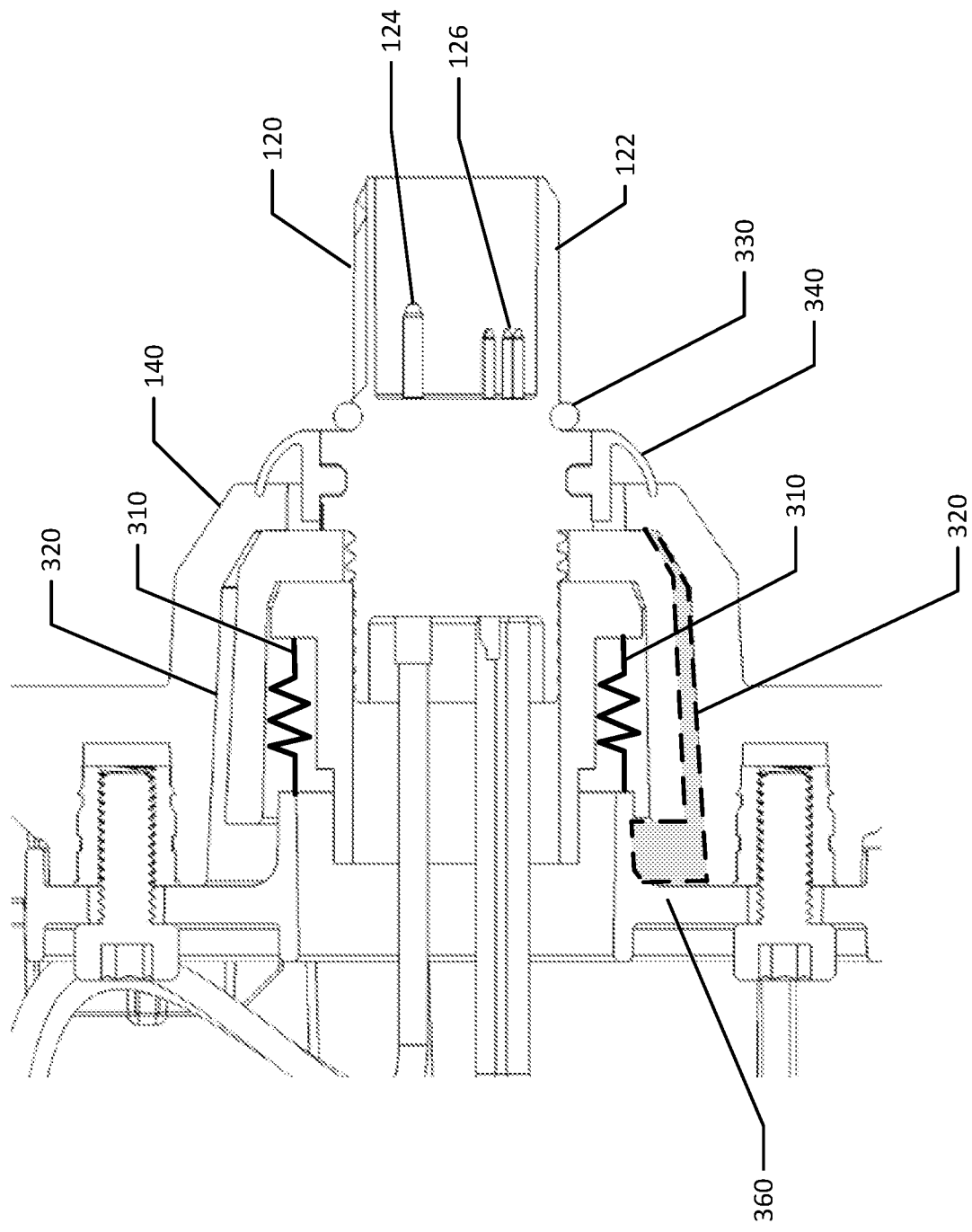
FIG. 3B is a cross-sectional view of the connector plug of FIG. 3A according to an example embodiment of the present disclosure.

FIG. 3B is a cross-sectional view of the connector plug 120 along line 3B-3B of FIG. 3A. The cross-sectional view illustrates that the connector plug 120 includes a cylindrical side-wall 122 and various connector pins 124, 126. As shown in FIG. 3B, the connector plug 120 is disposed within connector seal shell 140. The connector plug 120 is capable of moving in the X-direction or the Z-direction (e.g., along the X-axis and Z-axis), facilitated by the self-aligning connector system of the present disclosure. Within the connector seal shell 140, biasing member(s) 310 are provided to allow for alignment in the Z-direction (e.g., along the Z-axis). For example, biasing member(s) 310, such as biasing springs, may be compressed thereby allowing the connector plug 120 to move in the Z-direction to accommodate alignment in the Z-direction with the corresponding connector receptacle (e.g., connector receptacle 420 illustrated in FIG. 4) of the device 115. Specifically, compression of the biasing member(s) 310 and therefore compression of the connector plug 120 ensures proper engagement between the rack 110 and an associated medical device 115 in the Z-direction. Additionally, the biasing member(s) 310 may advantageously ensure that the seal formed by the connection is not overly compressed as the connector plug 120 is adapted to move in the Z-direction under sufficient pressure. As illustrated in FIG. 3B, the connector shell seal 140 or another corresponding structure on the rack 110 may include a backstop or capturing feature 360 that is adapted to capture the biasing member(s) 310.

The connector plug 120 may also include a sealing member 330, such as an O-ring positioned around a base of the connector plug 120 that is configured to form a seal between the connector plug 120 and a corresponding connector on the medical device 115. Additionally, the connector plug 120 may include a sealing flange 340 that forms a seal with connector shell seal 140 regardless of the axial position of the connector plug 120. For example, the sealing flange 340 may be adapted to ensure that the interface of the connector plug 120 and connector shell seal 140 are sealed from the environment when the connector plug 120 is in any of its axial-allowable positions (e.g., moved to its limit in any of the X-direction, Y-direction and the Z-direction (e.g., along the X-axis, the Y axis and the Z-axis).

Figure 4:
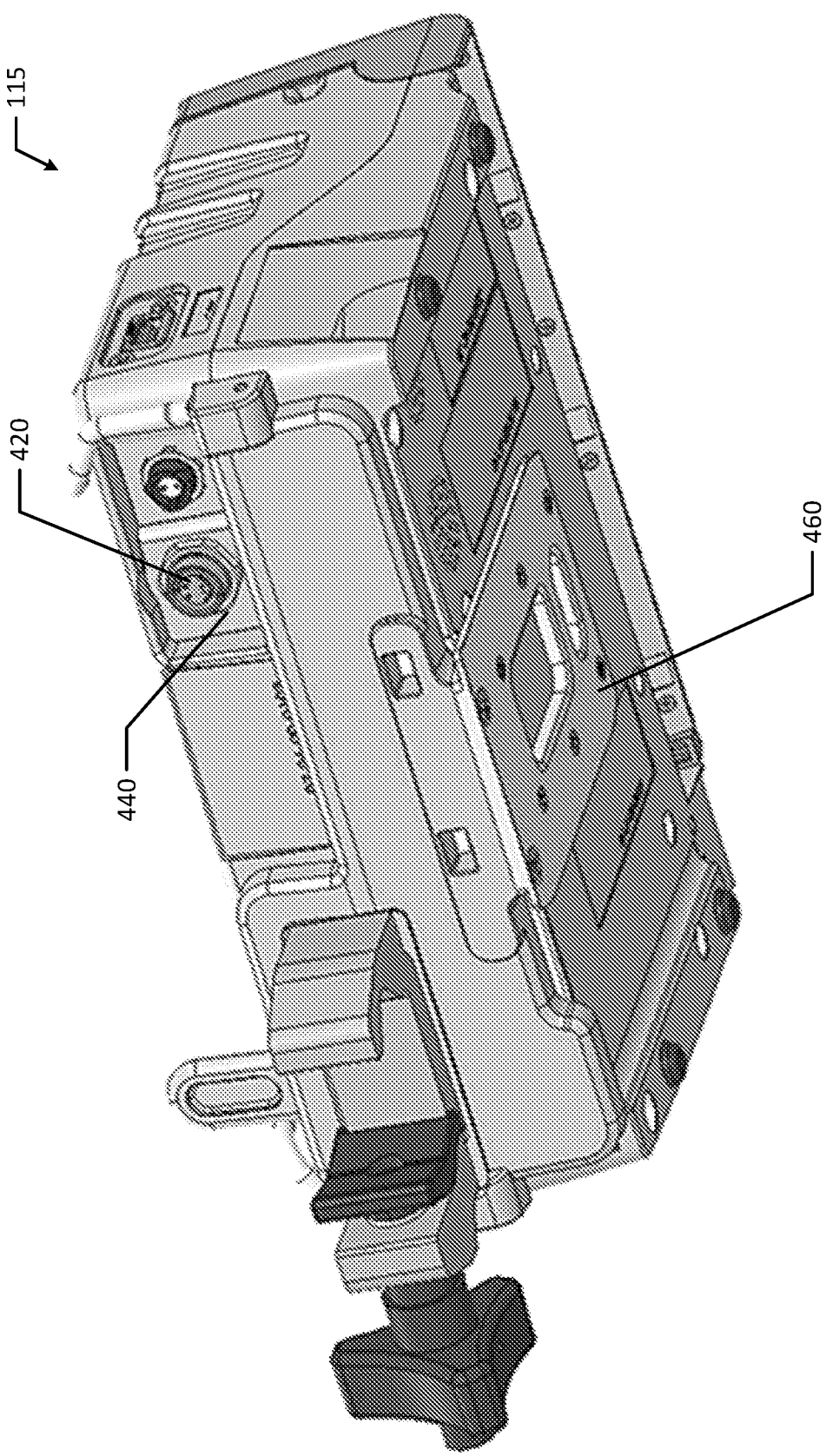
FIG. 4 is a perspective view of an example device operable with a rack according to an example embodiment of the present disclosure.

A spatial volume 320 is provided between the connector plug 120 and the connector seal shell 140, which provides the connector plug 120 spatial freedom or the ability to move in the X-direction, Y-direction and the Z-direction (e.g., along the X-axis, the Y axis and the Z-axis) while engaging the connector receptacle (e.g., connector receptacle 420 illustrated in FIG. 4). The spatial volume 320 may be a ring-shaped pocket that allows the connector plug 120 to move tri-axially within the connector seal shell 140 for proper alignment with a corresponding connector on a medical device 115. A portion of the spatial volume 320 is indicated by the dashed-outline and gray shading near the bottom portion of the connector plug 120 and connector seal shell 140. As illustrated in FIGS. 3A and 3B, the connector plug 120 and the connector seal shell 140 are configured an arrange in such a way that the connector plug 120 is retained within the connector seal shell 140 while being capable of moving tri-axially for alignment purposes. As mentioned above, the engagement is facilitated by the self-aligning connector system of the present disclosure.

FIG. 4 is a perspective view of an example medical device 115 that is configured to be operable with the rack 110 of the present disclosure. In an example, the medical device 115 is a medical pump, such as an infusion pump. As shown in FIG. 4, the device 115 includes a bracket 460, which may be fixed to the bottom of the device 115. The bracket 460 may be configured to be received by the shelf 260 of the rack 110. On the exterior of the device 115, a connector receptacle 420 is disposed within the connector seal 440. The connector receptacle 420 is configured to receive the connector plug 120 of the rack 110. Specifically, the connector receptacle 420 of the medical device 115 is configured to engage with the connector plug 120 of the rack 110. As discussed above, the position or orientation of the connector plug 120 may adjust tri-axially to ensure that the connector plug 120 is aligned with and properly engages the connector receptacle 420. The connector seal 240 is adapted to connect with the connector shell seal 140 of the rack 110 to provide a seal of the connection between the connector plug 120 and the connector receptacle 420.

Figure 5A:
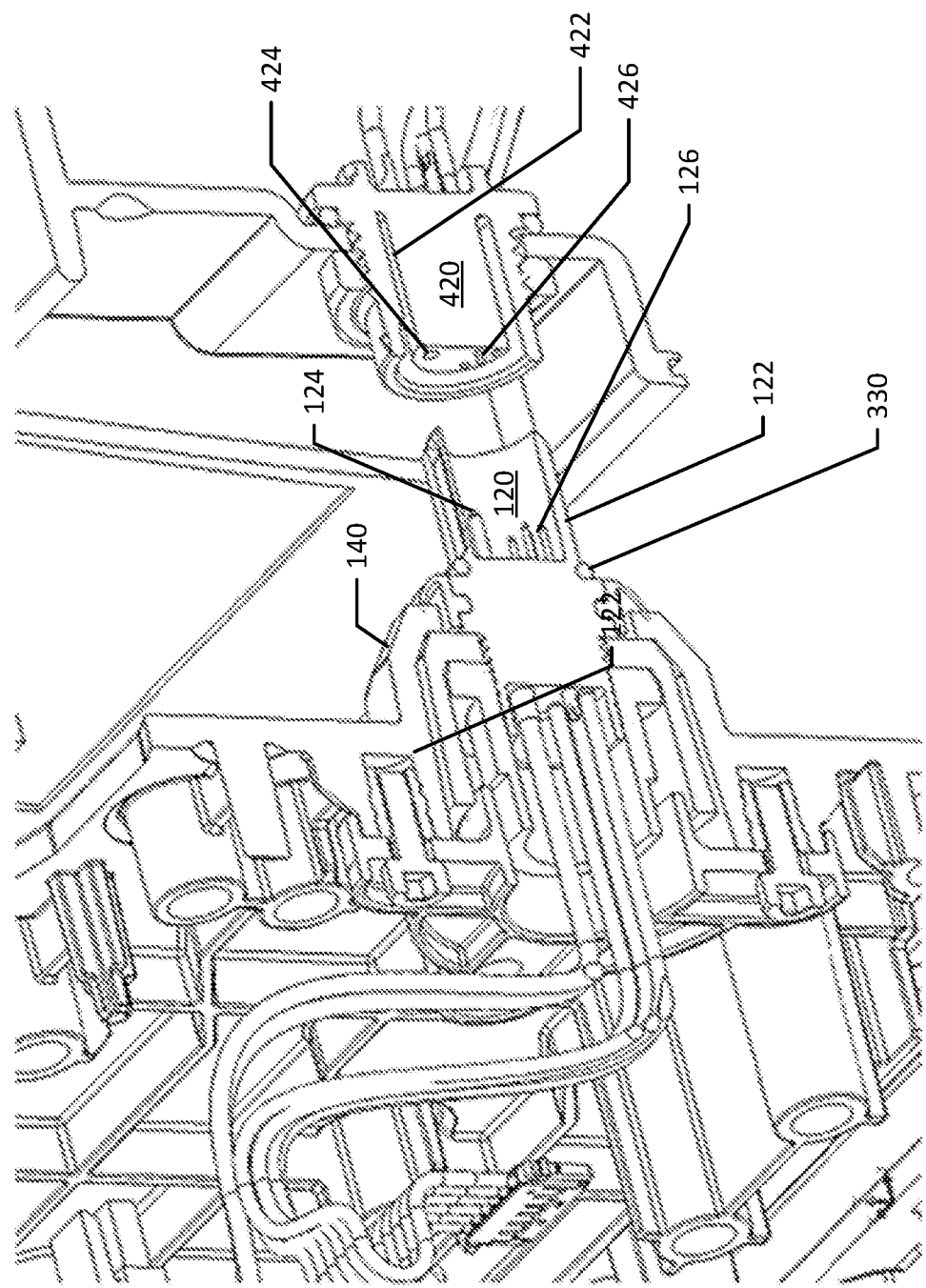
FIGS. 5A, 5B, 5C and 5D are cross-sectional views of the device and rack connection interfaces prior to and after engagement according to example embodiments of the present disclosure.
Figure 5B:
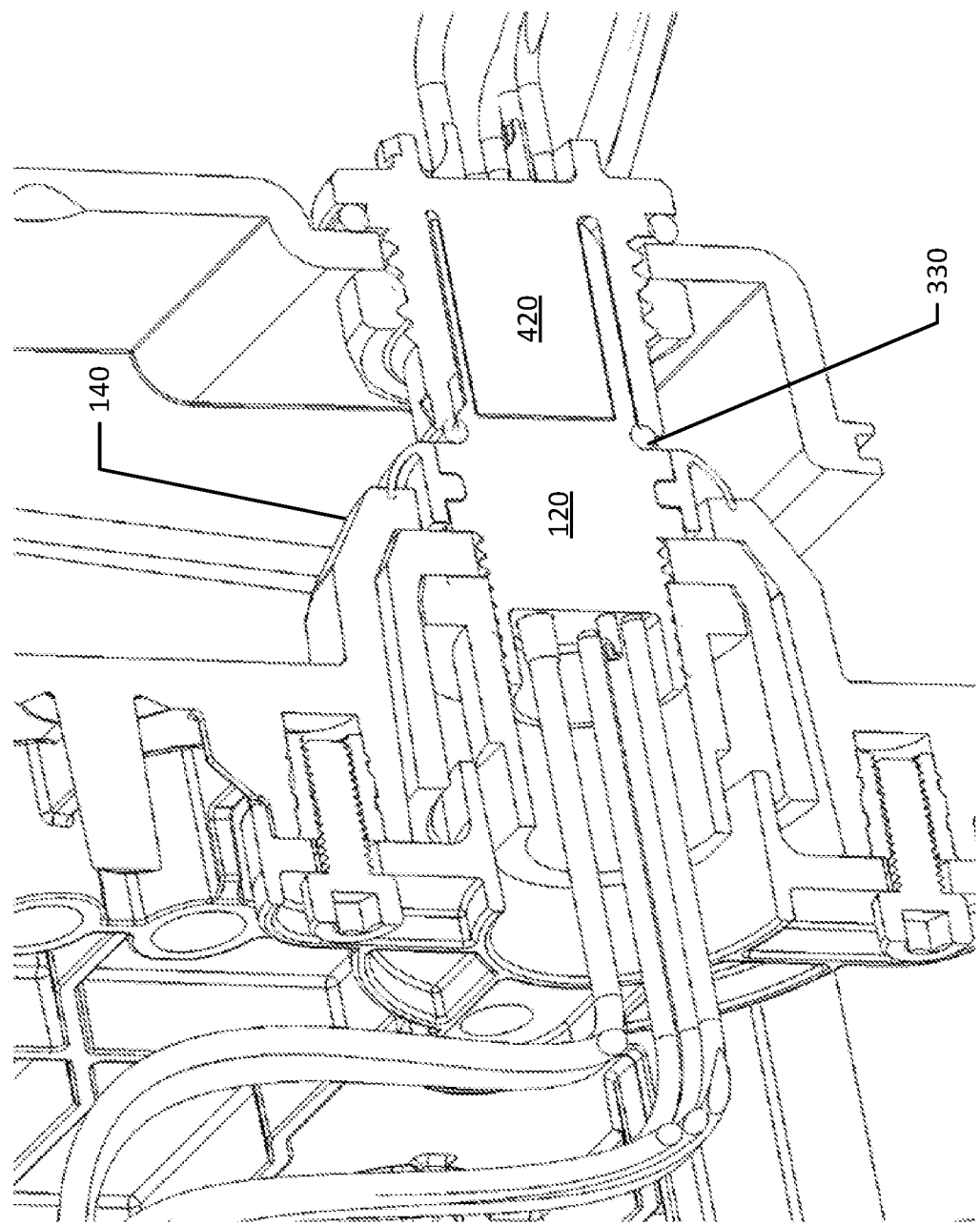

FIGS. 5A and 5B illustrate perspective cross-sectional views of the engagement between a medical device 115 and a rack 110 (prior to engagement in FIG. 5A and after full engagement in FIG. 5B). More specifically, FIG. 5A illustrates a perspective cross-sectional view of the engagement between the connector plug 120 and connector receptacle 420 aligned prior to engagement while FIG. 5B illustrates the connection interfaces after full engagement. As shown in FIGS. 5A and 5B, the device 115 is disposed on the rack 110 and the connections of both the rack 110 and device 115 are generally, spatially near each other and tri-axially aligned. More specifically, the connector plug 120 disposed within a connector shell seal 140 is in tri-axial alignment with the connector receptacle 420 disposed within the connector seal 440. Once the connections of both the device 115 and the rack 110 are disposed spatially near each other, the connector plug 120 will tri-axially self-adjust its spatial position based on the connector's axial needs including its seal. The tri-axially self-adjustments of the connector plug 120 allows for the connector plug 120 to make discrete movements in either the X-direction, the Y-direction and/or the Z-direction to ensure the connections or connection interfaces between the device 115 and the rack 110 are aligned. Specifically, tri-axial alignment advantageously ensures that the connector plug sidewall 122 fits within the corresponding channel 422 of the connector receptacle 420 and that connector pins 124, 126 engage their corresponding connector slots 424, 426 of the connector receptacle 420 on the medical device 115. Mating with the connector receptacle 420 on the device 115 side forces the connector plug 120 into its final position to minimize any misalignments in the system. Once the connector plug is in its final position, the sealing member or O-ring 330 forms a seal with connector receptacle 420 to seal channel 422 from the outside environment.

Figure 5C:
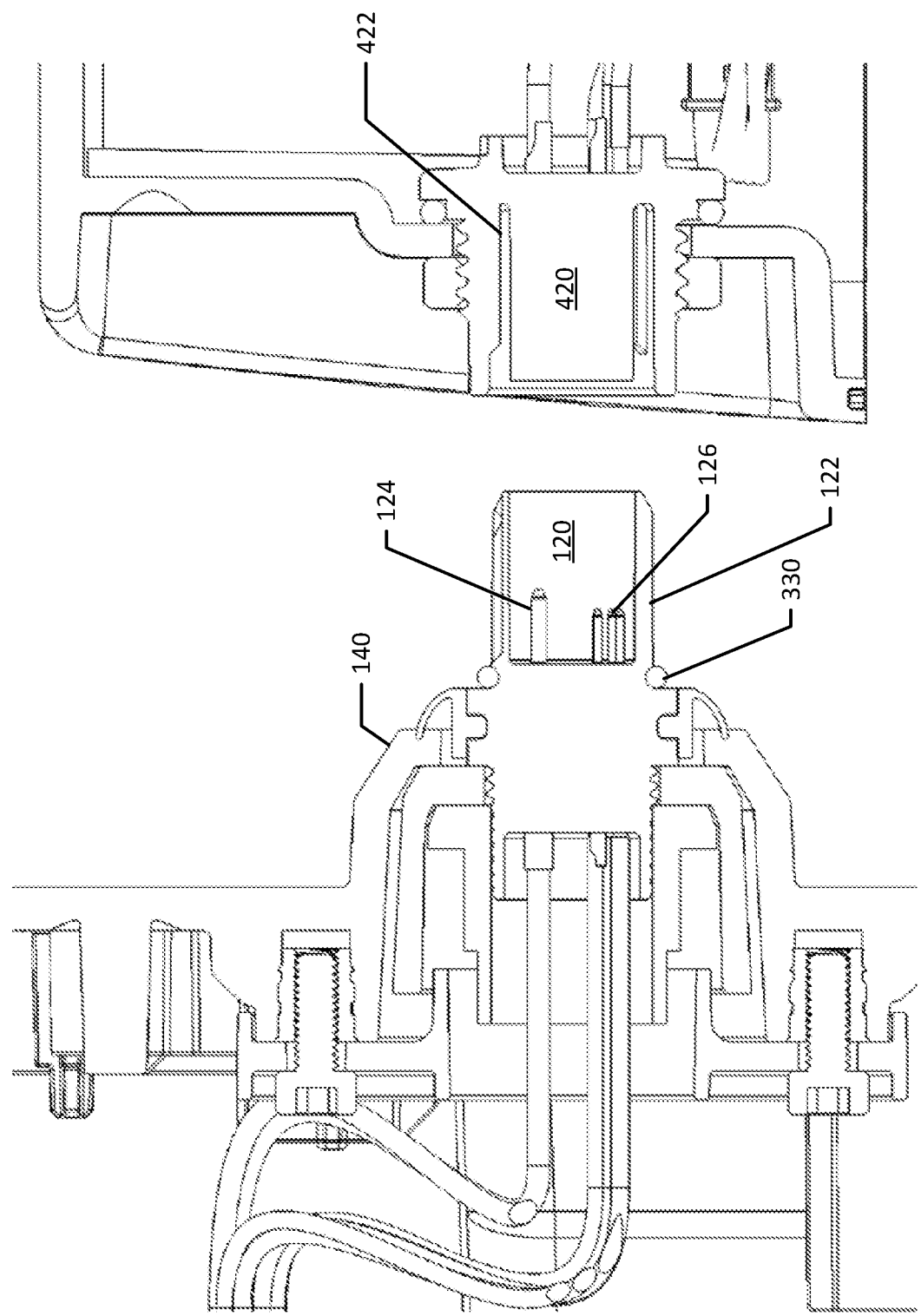
Figure 5D:
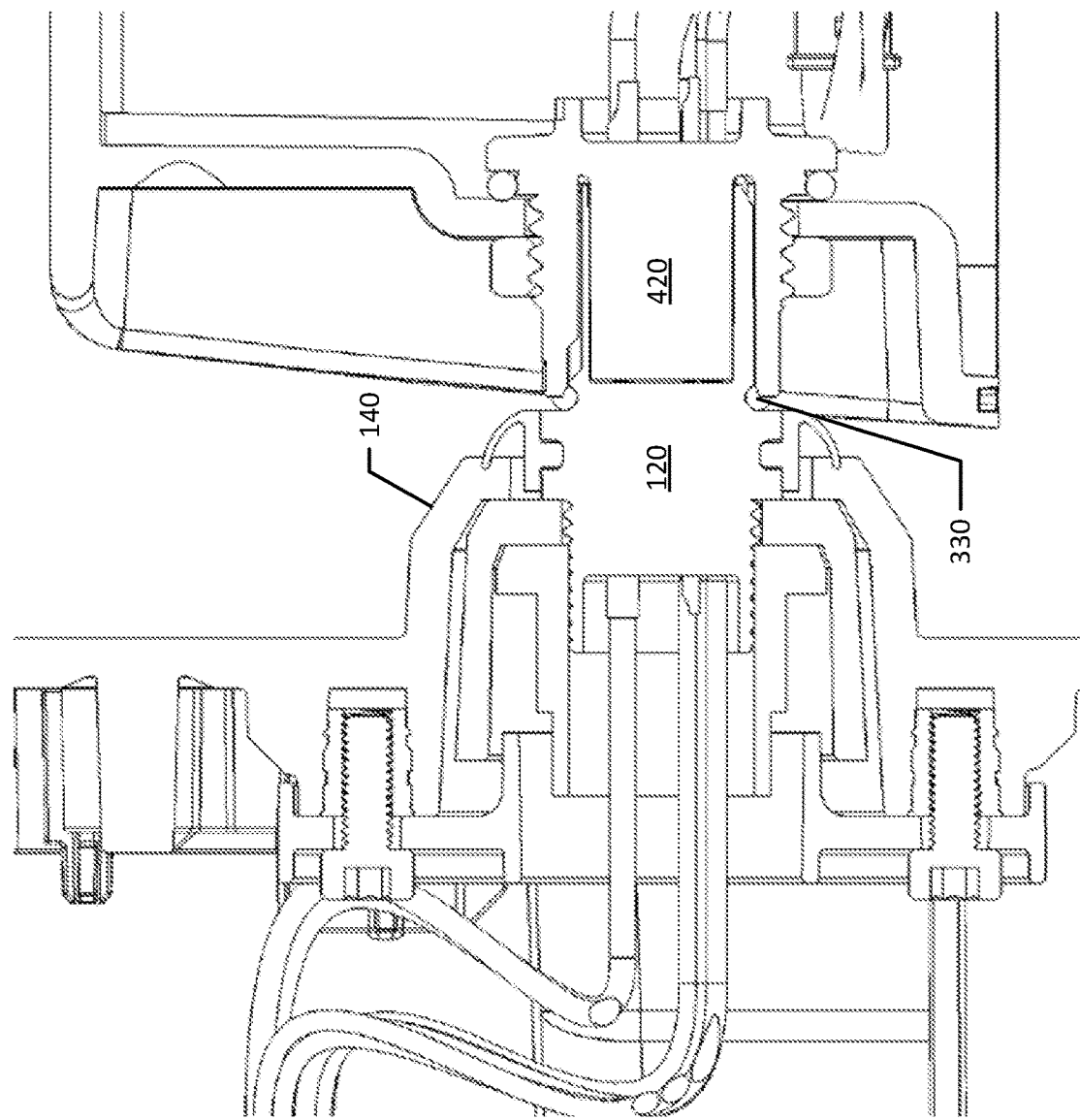

FIGS. 5C and 5D illustrate cross-sectional views of the engagement between a medical device 115 and a rock 110 (prior to engagement in FIG. 5C and after full engagement in FIG. 5D). As illustrated in FIGS. 5C and 5D, the connection interfaces of the rack 110 and medical device 115 are tri-axially aligned to ensure proper engagement. Self-alignment is complete when the connector seal shell 140 and the connector seal 440 engage to form a seal between the two connection interfaces. As the device 115 and its associated connector receptacle 420 move closer to the connector plug 120 and connector shell seal 140, the connector plug's sidewall 122 slides into the corresponding channel 422, which may initially be oversized for an initial alignment and then may be tapered to a final alignment position. As the connection interfaces engage, the connector plug 120 may be compressed in the Z-direction to ensure proper position along the Z-axis. Since the connector plug 120 is biased outward toward the corresponding connector receptacle 420 via the biasing member(s) 310, the sealing member 330 contacts and forms a seal with connector receptacle 420. In an example, the biasing member(s) 310 within the connector shell seal 140 ensures that the seal is not over-compressed as the plug 120 is capable of axially repositioning in the Z-direction.

When the connector plug 120 is mated with the connector receptacle 420 and a seal is achieved between the connection interfaces, the rack 110 and device 115 are able to communicate with each other. In some embodiments, the rack 110 and device 115 pass electrical signals between each other via the connection formed. In another embodiment, the rack 110 and device 115 are in fluid communication via tubing disposed within the connection formed and fluids are able to be passed between each other.

The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. For instance, any suitable combination of features of the various examples described is contemplated.

The invention is claimed as follows:

1. A self-aligning connection system comprising:
  a device comprising a connector receptacle configured to receive a connector plug, a connector seal and a bracket fixed to the device;

a modular rack comprising the connector plug, a connector shell seal and a shelf configured to receive the bracket and guide the shelf in a plurality of directions;

wherein when the bracket of the device is inserted into the shelf of the modular rack, the shelf travels in the plurality of directions to self-align the connector plug of the modular rack to the connector receptacle of the device to ensure engagement of the connector plug to the connector receptacle;

wherein in response to the connector receptacle initiating engagement with the connector plug, the connector plug travels in the plurality of directions to adjust a spatial position in relation to the connector receptacle; and wherein when the connector shell seal of the modular rack and the connector seal of the device are aligned, the connector seal is biased towards the connector shell seal to create a seal and ensure engagement of the connector plug relative to the connector receptacle.

2. The self-aligning connection system of claim 1, wherein the connector plug is disposed within the connector shell seal and a spatial volume is provided adjacent to the connector plug within the connector seal shell to allow for freedom of movement during self-alignment.

3. The self-aligning connection system of claim 1, wherein the device is a medical device.

4. The self-aligning connection system of claim 1, wherein the engagement between the device and the modular rack allows for an operable connection of at least one of an electrical connection, a data connection, a gas connection, and a fluid connection.

5. The self-aligning connection system of claim 1, wherein the connector seal is biased towards the connector shell seal to ensure engagement of the connector plug relative to the connector receptacle.

6. The self-aligning connection system of claim 1, wherein the plurality of directions includes an X-direction, a Y-direction and a Z-direction.

7. The self-aligning connection system of claim 1, wherein the shelf of the modular rack includes guide rails that are configured to retain and guide the bracket of the device.

8. A self-aligning connection system comprising:
a device comprising a connector receptacle configured to receive a connector plug, a connector seal and a bracket fixed to the device;
a modular rack comprising the connector plug, a connector shell seal and a shelf configured to receive the bracket and guide the shelf in a plurality of directions;
a guiding system with mechanical means for facilitating the movement of the bracket of the device in relation to the shelf of the modular rack without human intervention;
wherein when the bracket of the device is inserted into the shelf of the modular rack, the shelf travels in a plurality of directions to self-align the connector plug of the modular rack to the connector receptacle of the device to ensure engagement of the connector plug to the connector receptacle;
wherein in response to the connector receptacle initiating engagement with the connector plug, the connector plug travels in the plurality of directions to adjust a spatial position in relation to the connector receptacle; and
wherein when the connector shell seal of the modular rack and the connector seal of the device are aligned, the connector seal is biased towards the connector shell seal to create a seal and ensure engagement of the connector plug relative to the connector receptacle.

9. The self-aligning connection system of claim 8, wherein the connector plug is disposed within the connector shell seal and a spatial volume is provided adjacent to the connector plug within the connector seal shell to allow for freedom of movement during self-alignment.

10. The self-aligning connection system of claim 8, wherein the device is a medical device.

11. The self-aligning connection system of claim 8, wherein the engagement between the device and the modular rack allows for an operable connection of at least one of an electrical connection, a data connection, a gas connection, and a fluid connection.

12. The self-aligning connection system of claim 8, wherein the connector seal is biased towards the connector shell seal to ensure engagement of the connector plug relative to the connector receptacle.

13. The self-aligning connection system of claim 8, wherein the plurality of directions includes an X-direction, a Y-direction and a Z-direction.

14. The self-aligning connection system of claim 8, wherein the shelf of the modular rack includes guide rails that are configured to retain and guide the bracket of the device.

15. A method for connecting a device to a modular rack, the method comprising:
providing the device with a connector receptacle and a connector seal configured to receive a connector plug;
attaching a bracket to at least one surface of the device;
providing a modular rack with at least one shelf and at least one connector plug to provide an operable connection from the modular rack relative to the device;
inserting the bracket of the device in a shelf of the modular rack configured to receive the bracket; and
providing a guiding system operable with the modular rack with mechanical means for guiding and retaining the bracket of the device and moving the shelf in a plurality of directions, facilitating tri-axial self-alignment of the shelf in relation to the connector plug;
wherein the step of providing the device with the connector receptacle and the connector seal configured to receive the connector plug includes, in response to the connector receptacle of the device initiating engagement with the connector plug of the modular rack, the connector plug traveling in a plurality of directions to adjust a spatial position in relation to the connector receptacle to facilitate connection between the device and the modular rack.

16. The method of claim 15, including biasing the connector seal towards the connector shell seal to ensure engagement of the connector plug relative to the connector receptacle.

17. The method of claim 15, wherein the operable connection is at least one of an electrical connection, a data connection, a gas connection, and a fluid connection.

18. The method of claim 15, wherein the method is performed without human intervention.

19. The method of claim 15, wherein the device is a medical device.

20. The method of claim 15, wherein the plurality of directions include an X-direction, a Y-direction and a Z-direction.

* * * * *